United States Patent [19]
Powers

[11] Patent Number: 5,119,833
[45] Date of Patent: Jun. 9, 1992

[54] COMPRESSIBLE FOAM EARPLUG

[75] Inventor: William R. Powers, Newark, Del.

[73] Assignee: Argus Corporation, Newark, Del.

[21] Appl. No.: 669,894

[22] Filed: Mar. 15, 1991

[51] Int. Cl.⁵ .......................................... A61F 11/00
[52] U.S. Cl. ..................................... 128/865; 128/857
[58] Field of Search ............................... 128/864–868, 128/857

[56] References Cited

U.S. PATENT DOCUMENTS

| | | | |
|---|---|---|---|
| 4,253,452 | 3/1981 | Powers et al. | 128/864 |
| 4,459,247 | 7/1984 | Rothemund | 128/864 X |
| 4,552,137 | 11/1985 | Strauss | 128/864 |
| 4,579,112 | 4/1986 | Scott | 128/864 |
| 4,774,938 | 10/1988 | Leight | 128/864 |

FOREIGN PATENT DOCUMENTS

| | | | |
|---|---|---|---|
| 0108728 | 5/1984 | European Pat. Off. | 128/864 |
| 2817809 | 9/1979 | Fed. Rep. of Germany | 128/864 |

Primary Examiner—Robert A. Hafer
Assistant Examiner—Brian E. Hanlon
Attorney, Agent, or Firm—Connolly & Hutz

[57] ABSTRACT

A compressible earplug is made of a slow recovery foam material. The earplug has a cross-section formed by a plurality of three or four sides wherein there is an angle no greater than 90° between at least two sets of adjoining sides. In this manner, the plug can be cut from a sheet of material with virtually no waste resulting. Preferably a linear saw cut is used for form the plugs.

14 Claims, 1 Drawing Sheet

COMPRESSIBLE FOAM EARPLUG

BACKGROUND OF INVENTION

The growing concern for noise pollution has lead to various types of ear protection devices. One type of device which has found great success is a foam earplug. For example, foam earplugs are known which are made of slow recovery material so that the earplugs can initially be of a cross-sectional area larger than the ear canal and then twirled and compressed to a cross-sectional area smaller than the ear canal to facilitate the insertion of the earplug into the ear. After the twirling has ceased the earplug begins to return to its original shape. Because of its slow recovery characteristic, however, sufficient time remains to permit the earplug to be inserted into the ear whereupon the earplug is effectively seated in the ear without reaching its fully relaxed dimensions.

The conventional shape for such slow recovery foam earplugs is of a circular cross-section as from a cylindrical shape. This shape was selected, apparently, because it would offer no corners which might irritate or cause discomfort to the wearer. In the manufacture of such earplugs by punching from a sheet, a great deal of waste material results because of the circular shape of the earplugs.

A variation of the cylindrical earplug is an earplug having a hexagonal cross-section. Here again, a hexagon appears to have the advantage of having its sides meet at such large angles to each other that there is thought to be minimal discomfort to the wearer. Theoretically, hexagonal earplugs could be punched from a sheet with no waste material resulting. In practice, however, it is found that severe compression accompanies the punching operation as it does with circular cross-section earplugs which causes membrane rupture between the foam cells. This reduces air flow resistance and deteriorates the sound attenuating properties of the foam. Still further, when such foam is compressed for punching portions often fail to compress uniformly which results in malformed plugs causing waste and necessitating a close inspection of the product.

SUMMARY OF INVENTION

An object of this invention is to provide a compressible slow recovery earplug which overcomes the above disadvantages.

A further object of this invention is to provide such an earplug which can be manufactured with minimal waste.

A still further object of this invention is to provide such an earplug which avoids the disadvantages of the prior art attendant to punching operations.

In accordance with this invention the earplug is made of a compressible slow recovery foam material wherein the earplug body has a cross-section in the form of four or less sides. Such cross-section may be a triangle, parallelogram, square, rectangle, trapezium or trapazoid. Thus a characteristic of the cross-section is that at least two sets of adjacent sides form an angle of 90° or less.

The earplugs are preferably made from a sheet of foam material by using a linear knife edge saw to perform the cuts without causing severe compression of the material and with virtually no waste resulting from such cuts.

THE DRAWINGS

DETAILED DESCRIPTION

The present invention is based upon the recognition that slow recovery foam could be used for manufacturing earplugs having flat sides which join at relatively shallow angles of 90° or less and which can be inserted into the ear without any particular discomfort to the wearer. This recognition is based upon the realization that when such slow recovery foam earplugs are placed in a condition for insertion into the ear, the earplugs are twirled so as to reduce their cross-sectional area to a size less than the ear canal and such twirling operation discounts whatever cross-sectional shape the earplug may have originally had. Since relatively soft materials are used, when the earplugs tend to resume their normal condition there are sharp discomforting corners. This realization makes possible the formation of earplugs having only three or four sides so that the earplugs can be conveniently manufactured from a sheet of foam material with virtually no waste resulting.

Figure 1:
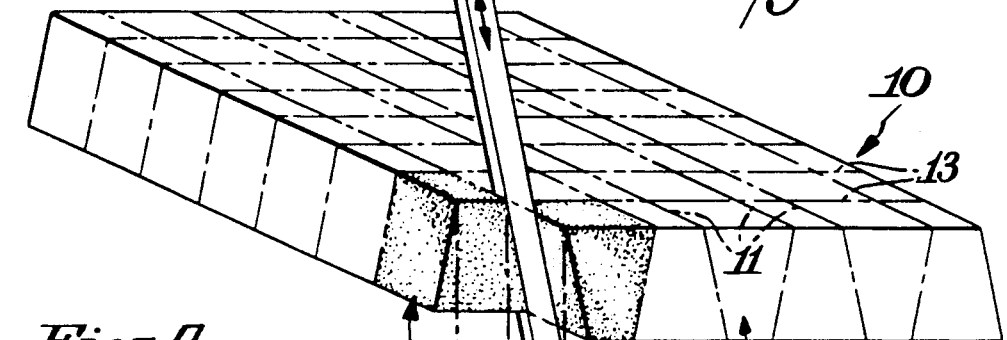
FIG. 1 is a perspective exploded view of a sheet of foam material having earplugs formed therefrom in accordance with this invention.

FIG. 1 illustrates a sheet of material 10 made of a suitable slow recovery foam material such as the foams disclosed in U.S. Re 29,487. It is preferable, however, that polyurethane foam be used for manufacturing the earplugs. Sheet 10 is theoretically divided by column lines 11 and row lines 13 into a number of individual earplugs 12 having a tapered rectangular shape as better illustrated in FIGS. 2-4. The tapered shape permits each column of earplugs to be inverted with respect to its adjacent column as clearly shown in FIG. 1.

The earplugs are preferably formed by the use of linear saw cuts which is schematically illustrated by the cutting saw blade 15 of FIG. 1. Such form of manufacture lends itself to high speed operation which does not compress the foam. Moreover, as is readily apparent from FIG. 1, the tapered plugs have a trapezoidal cross-section that can be cut without waste. The resultant rectangular or square cross-section is a four sided figure wherein the angle of each pair of adjacent sides is 90°.

Figure 4:
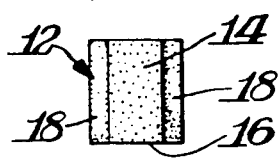
FIG. 4 is a top plan view of the earplug shown in FIGS. 2-3.
Figures 2, 3:
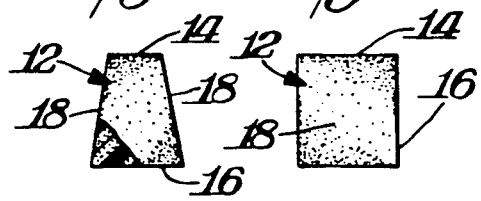
FIG. 2 is a end elevational view, partly in section, of a tapered rectangular earplug in accordance with this invention.
FIG. 3 is a side elevational view of the earplug shown in FIG. 2.

As best shown in FIGS. 2-4 plug 10 thus includes a narrow end 14 of, for example, rectangular cross-section and a symmetrically disposed wide end 16 with tapered sides 18. If desired, narrow end 14 may be offset with respect to widened end 16 rather than being symmetrically arranged.

Because only linear sawing are used for forming the individual plugs 12 from the parent sheet 14, there is no severe compression which accompanies the punching operation used heretofore when round or hexagonal plugs possessing a taper are punched from a sheet. Accordingly, the linear saw cuts used in the production of earplugs in accordance with this invention avoids the disadvantage of the prior art punching techniques since such prior art punching techniques result in a reduction of air flow resistance with a deterioration of the sound attenuating properties of the earplugs. Additionally, the linear saw cuts operation avoids the disadvantage attendant with punching operations wherein there is a failure to compress uniformly with such punching operations thereby resulting in malformed plugs causing waste and necessitating a close inspection of the product.

Figure 5:
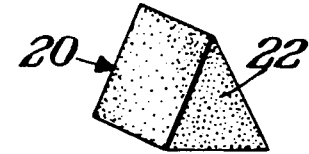
FIG. 5 is a perspective view of an earplug having a triangular cross-section in accordance with this invention.
Figure 6:
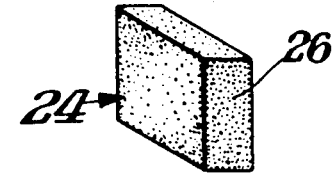
FIG. 6 is a perspective view of an earplug having a rectangular cross-section in accordance with this invention.

FIG. 5 illustrates a variation of the invention wherein an earplug 20 is formed having a triangular cross-section 22. As illustrated, the sides forming the triangle include at least two angles of less than 90°. FIG. 6 illustrates a further variation wherein an earplug 24 is formed having a parallelogram cross-section 26.

Figure 7:
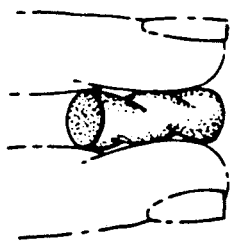
FIG. 7 is a perspective view showing the manner of preparing an earplug for insertion into the ear in accordance with this invention.

As is apparent the earplugs may be cut from the parent sheet of material in any suitable cross-section wherein the resultant plug has three or four sides which would include a triangle, square, rectangle, parallelogram, trapezium or trapazoid. Characteristic of such earplug is that at least two sets of adjacent sides form angles of 90° or less. As illustrated in FIG. 7 the sharp edges resulting from such perpendicular or acute angles are discounted when the earplug is twirled to be conditioned for insertion into the ear. For example, with such practice the user would place the plug P between the thumb and forefinger and twirl or roll the plug so as to reduce its cross-sectional size and in effect form a generally cylindrical member. This generally cylindrical member results regardless of the original configuration or cross-sectional shape of the plug. The reduced plug can then be easily inserted into the ear canal where it expands to cause complete obturation.

Any suitable dimensions and materials may be used for the practice of this invention. The cross-sectional area of an uncompressed foam plug may thus vary over a wide range depending upon the uncompressed void-volume/polymer-volume ratio (the porosity) and the resistance to air flow of the foam employed. Typically, the cross-sectional area will range from 0.15 to 0.50 square inches. The length of an earplug may range from 0.375 to 1 inch.

The earplugs may have a cross-section which is uniform in dimension throughout its length or may be tapered in length. Where a tapered plug is used, and when the plug is twirled and compressed the result is the formation of a cone or truncated cone. The small end of the cone facilitates insertion into the ear canal.

Earplugs having a rectangular cross-section can be manufactured with a very substantial reduction in wasted material compared for example to an earplug of circular cross-section. In this respect, when circles are punched from a sheet, the absolute minimal waste is 21.5% if the circular cuts are tangential. With foam it is necessary, however, to leave a space between each punch so that typically the waste runs 30-40%. Although nested hexagonal earplugs may theoretically be made without waste, as a practical matter, the edge effects cause a considerable loss. When, however, in accordance with the invention the earplug has only three or four sides and linear saw cuts are used, the waste is virtually eliminated. It is estimated that the foam material consumed cutting a tapered rectangular plug would be only about 40% of that consumed in producing a punched cylindrical plug.

What is claimed is:

1. A compressible earplug comprising a body made from a slow recovery foam material capable of being reduced in cross-sectional size by twirling and slowly tends to return toward its original size, said body having a flat planar base, a plurality of flat planar sides extending upwardly from said base, said plurality of sides comprising no more than four sides, adjacent pairs of said sides forming corners, and said sides for at least two of said corners forming an angle which is no greater than 90°.

2. The earplug of claim 1 wherein said body is tapered in length.

3. The earplug of claim 1 wherein said plurality of sides form a triangle.

4. The earplug of claim 1 wherein said plurality of sides form a square.

5. The earplug of claim 1 wherein said plurality of sides form a rectangle.

6. The earplug of claim 1 wherein said plurality of sides form a parallelogram.

7. The earplug of claim 1 wherein said plurality of sides form a trapezium.

8. The earplug of claim 1 wherein said plurality of sides form a trapazoid.

9. The earplug of claim 1 wherein said cross-section has an area in the range of 0.15-0.50 square inches and said body having a length in the range of 0.375-1 inch.

10. A method of forming a plurality of compressible earplugs comprising the steps of providing a parent sheet made from a slow recovery foam material capable of being compressed and then slowly returning toward its original uncompressed shape, and making a series of linear saw cuts completely through the parent sheet to form individual earplugs having a flat base and no more than four planar sides with the angle formed by at least two sets of adjacent sides being no more than 90°.

11. The method of claim 10 wherein the series of cuts are rows and columns.

12. The method of claim 11 wherein the earplugs are tapered in length.

13. The method of claim 12 wherein all of the earplugs in each column are inverted with respect to all of the earplugs in its adjacent column.

14. The method of claim 10 wherein the sides form an area in the range of 0.15-0.50 square inches and each earplug has a length in the range of 0.375-1 inch.

* * * * *